United States Patent [19]

Yasnitsky et al.

[11] 4,159,334
[45] Jun. 26, 1979

[54] MEDICINAL PREPARATION WITH AN ANTIINFLAMMATORY, ANALGESIC AND ANTIPYRETIC EFFECT

[76] Inventors: Boris G. Yasnitsky, Rogatinsky pereulok, 6, kv. 1; Yaroslav I. Khadzhai, prospekt Lenina, 48A, kv. 36; Galina V. Obolentseva, ulitsa Prodolnaya, 3B, kv. 28; Elena B. Dolberg, ulitsa Sumskaya, 77/79, kv. 135; Alexandra I. Vidjukova, prospekt Traktorostroitelie, 102, kv. 2; Tatyana V. Medvedeva, Saltovskoe shosse, 139V, kv. 43; Nina A. Bugrim, Moskovsky prospekt, 214/2, kv. 59; Viktor P. Georgievsky, ulitsa Prodolnaya, 3B, kv. 49, all of Kharkov, U.S.S.R.

[21] Appl. No.: 838,715

[22] Filed: Oct. 3, 1977

[51] Int. Cl.$^2$ ............................................. A61Q 31/425
[52] U.S. Cl. ........................................................ 424/270
[58] Field of Search ............................................ 424/270

[56] References Cited

PUBLICATIONS

Chem. Abst. 76-85739q (1972).

*Primary Examiner*—Stanley J. Friedman
*Attorney, Agent, or Firm*—Lackenbach, Lilling & Siegel

[57] ABSTRACT

A medicinal preparation with an antiinflammatory, analgesic and antipyretic effect, comprising 2,2,2-trichloro-1-(2-thiazolyl amino)-ethanol as the active principle, which has the following formula:

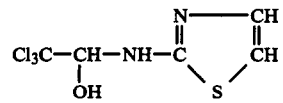

and an appropriate pharmaceutical carrier.

The preparation is used for the treatment of various diseases, for example: rheumatism in the active phase, rheumatoid, infectious allergic and metabolic arthritis, spondyloses and arthroses, lumbosacral radiculitis, and others.

4 Claims, No Drawings

MEDICINAL PREPARATION WITH AN ANTIINFLAMMATORY, ANALGESIC AND ANTIPYRETIC EFFECT

The present invention relates to medicine, specifically to a new preparation with an antiinflammatory, analgesic and antipyretic effect for the treatment of various inflammatory diseases.

According to the invention, the new medicinal preparation for the treatment of inflammatory diseases comprises, as the active principle, 2,2,2-trichloro-1-(2-thiazolyl amino)-ethanol with the following formula:

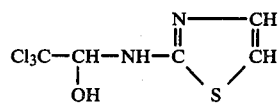

in combination with a pharmaceutical carrier.

The proposed medicinal preparation finds application in the treatment of various diseases, for example: rheumatism in the active phase (1st to 3rd degree), rheumatoid and infectious allergic arthritis, metabolic arthritis, different spondyloses and arthroses, lumbosacral radiculitis, and others.

The proposed preparation was examined pharmacologically. It wash established in acute tests in mice with carrageenin and aerosol-induced inflammatory edema (in experimental models most adequate to the inflammatory process in human rheumatism), that the proposed preparation, in single oral doses of 5 to 20 mg/kg, reduces the symptoms of exudation by 17-62%, which is three times superior to the action of acetylsalicyclic acid.

In subacute tests in rats, the preparation given in 10 mg/kg doses produces a pronounced effect on the dynamics of the exudative process, reducing its intensity by half within 3 hours after administration and maintaining this effect for four days. Acetylsalicylic acid under the same test conditions produces a similar effect, but with a dose 30 times higher than the dose of the proposed preparation.

It was established in tests with rats with implanted sterile paper rolled into balls that 10 and 20 mg/kg doses of the preparation reduce the weight of the granulomas by 41-60% and, consequently, produce an inhibiting effect on proliferation processes during inflammation.

An essential role in the antiflammatory action of the preparation is played by its membrane-stabilizing effect, which we discovered during in vitro and in vivo tests by the mitigation of the erythrocyte aggregation reaction, caused by a gelatine solution. Test results obtained in adrenalectomized animals, prompt the assumption that the andrenal system contributes to the proposed preparation's antiinflammatory effect.

The proposed preparations's analgesic effect was proved by three methods: in mice by the tail burning test and acetic acid "writhing"; in rats by painful irritation with electric current. For example, the preparation introduced orally to mice in 10 and 20 mg/kg doses reduced the reaction of the mice to a thermal irritant by 47-75% an hour after administration. Acetylsalicylic acid in 40-300 mg/kg doses causes an effect equal to 37-87%. A comparison of the $ED_{50}$ values of the proposed preparation and acetylsalicylic acid obtained in the three models, showed that the proposed preparation is from 3.5 to 15 times more active.

Tests in rats with yeast fever showed 50 and 100 mg/kg doses of the preparation to render an antipyretic effect, lowering body temperature by 1°-1.5° C. The effect of the preparation in a 100 mg/kg dose corresponds to that produced by a 300 mg/kg dose of acetylsalicylic acid. Mice given the same dose of the preparation followed by the administration of phenamine do not manifest the usual hyperthermia.

The proposed preparation was tested for acute toxicity in cats and mice. Symptoms of intoxication and death occur in cats following the administration of doses in excess of 1 g/kg. The picture of intoxication develops against the background of pronounced inhibition in the animals into a state similar to the prenarcotic state.

The preparation's $LD_{50}$ in mice given it orally is 1048(919 to 1,195) mg/kg, intraperitoneally, 708(575 to 871) mg/kg; that of acetylsalicylic acid given orally, 1,906(1,191 to 3,049) mg/kg; intraperitoneally, 1,097(795 to 1,514) mg/kg. It should be noted that the enteral coefficient for the proposed preparation is 1.48, and for acetylsalicylic acid —1.8, which indicates the better absorption of the preparation from the gastrointestinal tract.

The proposed preparation is well tolerated by rats, rabbits and dogs during oral administration in different doses for 2 to 4 months. These doses, which are conventionally therapeutic, and equal to 5% of the $LD_{50}$ for these animals, exceeded 30 and 70 times the dose recommended for humans.

The preparation does not affect the function of the liver (bromsulphalein test), the kidneys (indigo carmine excretion rate), the peripheral blood composition, the functions of the respiratory and cardiovascular systems, nor does it essentially influence the secretory and motor function of the gastrointestinal tract, or cause changes in the weight and structure of the animals' internal organs.

The preparation does not cause irritation of tissues when applied to the conjunctive eye of rabbits, nor does it have any toxic effect on the cells of the amnionic membrane in a human tissue subculture.

The preparation was examined for possible embryotoxic effects in rats. For this purpose, rats were administered the proposed preparation for 12 days in a 55 mg/kg dose, equal to 5% of the $LD_{50}$, beginning from the 9th day of pregnancy. These tests established that the proposed preparation does not affect the development of the rat embryos. At the same time, parallel comparative tests established that acetylsalicylic acid produces an embryotoxic effect.

The proposed preparation was subjected to clinical trials in 251 patients in a number of clinics.

The method of treatment consisted in oral administration of the proposed preparation in tablet form in 0.1 to 0.2 g doses three times a day before meals. The daily dose did not exceed 0.6 g per patient. The course of treatment lasted 3 to 4 weeks. In individual cases, the preparation was given once daily for 1 to 5 days as a symptomatic remedy (analgesic and antipyretic).

The main group of the patients given a course of treatment (203 persons), had the following diseases: rheumatism (active phase, 1st-2nd degree, according to A. I. Nesterov's classification) affecting the joints and heart (primary and recurrent rheumocarditis, heart disease of rheumatic etiology with symptoms of cardiac decompensation, of the 1-2A degree)—76 patients; polyarthritis (rheumatoid, exacerbation of chronic infectious, acute infectious-allergic, metabolic)—89 patients; arthrosis, spondylosis, exacerbation of chronic interstitial pneumonia—9 patients.

The duration of disease in patients with rheumatism and rheumatoid arthritis was from 1.5 to 40 years.

The effectiveness of the preparation was assessed by changes in complaints, clinical observation results (temperature, sensation of pain, local manifestations of the inflammatory process) and laboratory examination data (changes patients' peripheral blood picture, albumin fractions, glycoproteins and sialic acids content in blood serum, examination of stools for occult blood before and after treatment, etc.).

The therapeutic effect of the proposed preparation became manifest on the 4th to 9th day from the beginning of treatment, with the improvement of the patient's general status, increasing physical activity, abatement of symptoms of local inflammation. A drop in temperature was observed towards the end of the first week of therapy. Following a 3 to 4 week course the temperature completely normalized.

In the group of patients with rheumatic heart and joint disease, the symptoms of polyarthritis disappeared completely by the 10th to 12th day of treatment in the majority of patients, pain in the region of the heart abated, ECG indices improved: extrasystole disappeared, symptoms of myocardial anoxia diminished.

The marked clinical improvement was accompanied by positive changes in paraclinical data: disappearance of leukocytes drop of the ESR to normal, a marked tendency towards a higher albumin content and the normalization of the gamma-fraction of the blood.

Along with the favorable effect of the proposed preparation on the acute-phase reactions and functions of the rheumatic patients' cardiovascular system, an improvement of their neurological status was observed, manifested by diminishing asthenia and irritability.

A pronounced therapeutic effect was observed in 80% of the rheumatic patients (in 61 out of the 76 patients), and in 68% of patients with arthritis of different etiology (61 out of 89). A similar effect was produced by the preparation in patients with arthrosis, spondylosis and exacerbation of chronic interstitial pneumonia (65%).

Clinicians hold the option that tolerance to the preparation is good. Its administration in courses of treatment showed no influence on the peripheral blood composition; on the contrary, a normalizing effect on the leukocyte count was observed: it diminished to norm in leukocytosis and increased in leukopenia, as testified by data in the following Table 1.

Table 1

| No | Hemoglobin, units, before/after treatment | erythrocytes, mln before/after treatment | leukocytes, thou before/after treatment |
| --- | --- | --- | --- |
| 1 | 2 | 3 | 4 |
| 1 | 79/79 | 4.650/4.190 | 4,400/8,200 |
| 2 | 81/84 | 5.040/4.330 | 6,000/8,700 |
| 3 | 76/79 | 4.050/4.780 | 8,900/5,400 |
| 4 | 72/76 | 4.500/7.720 | 8,500/6,250 |
| 5 | 66/74 | 3.650/4.260 | 5,800/5,650 |
| 6 | 78/74 | 4.270/4.210 | 5,100/5,750 |
| 7 | 74/77 | 4.520/4.300 | 5,000/5,700 |
| 8 | 71/70 | 3.660/4.000 | 3,800/4,700 |
| 9 | 69/70 | 3.500/3.900 | 5,000/10,000 |
| 10 | 71/76 | 3.980/4.430 | 3,600/4,200 |
| 11 | 65/72 | 3.540/4.250 | 6,800/7,100 |
| 12 | 67/62 | 4.418/3.750 | 7,450/7,000 |
| 13 | 60/64 | 4.000/4.180 | 4,000/6,400 |
| 14 | 79/72 | 4.300/4.000 | 5,750/5,600 |
| 15 | 79/72 | 4.300/4.000 | 4,600/5,500 |
| 16 | 79/72 | 4.300/4.000 | 10,000/6,600 |

The proposed preparation differs by its action from a number of medicinal remedies used for the therapy of inflammatory diseases. The above-described experimental studies demonstrate that the proposed preparation possesses higher activity than acetylsalicylic acid (see Table 2).

Table 2

| Effect | Experimental method | Relative activity of acetylsalicylic acid | proposed preparation |
| --- | --- | --- | --- |
| Anti-inflammatory | Aerosol-induced edema of paw in mice (acute test) | 1 | 3.2 |
| | Aerosol-induced edeima of paw in rats (subacute test) | 1 | 30.0 |
| Analgesic | Painful irritation of rat's paw with electric current | 1 | 15 |
| | Burning tail of mice | 1 | 9 |
| | Acetic acid "writhing" in mice | 1 | 3.5 |
| Antipyretic | Yeast fever in rats | 1 | 3 |
| | Phenamine hyperthermia in mice | 1 | 2.5 |
| Therapeutic index | Acute toxicity to anti-edematous action ratio ($LD_{50}/ED_{50}$) in mice, oral administration | 1 | 2 |

As Table 2 shows, the proposed preparation is superior to acetylsalicylic acid in all the main effects. Besides, the preparation offers the advantage of having a double therapeutic range. A comparison of the proposed preparations antiinflammatory effect through the test of carrageenin-induced inflammatory edema with the data available in the literature, reveals that the antiinflammatory activity of the new preparations is higher than that of sodium salicylate, phenylbutazone, mephenamic acid (Ponstan) and brufen.

The proposed preparation has a substantial advantage over acetylsalicylic acid, phenylbutazone, indometacin, brufen, ibuprophen and other non-steroidal antiinflammatory substances, in that, according to experimental data, it has no harmful effect on the gastrointestinal mucosa in doses either conventionally therapeutic, or doses exceeding them 10 and 20 times, during single or lasting administration (for four months).

On the basis of these experimental data, the preparation was used clinically for the treatment of patients with chronic polyarthritis accompanied by gastrointestinal pathology, namely duodenal ulcer in the stage of remission. The course of treatment did not cause an exacerbation of the ulcerous disease. The fecal reaction to occult blood was negative in all the patients. In view of the above, and also in view of the new preparation's general good tolerance, it may be used in patients with accompanying diseases of the organs of the alimentary system, which are contraindications to the use of most of the antiinflammatory remedies.

A comparison of the pharmacotherapeutic properties of the proposed preparation and of brufen shows that in the experiment the proposed preparation is 1.5 to 2 times less toxic than brufen. In contrast to brufen, it exhibits a moderately pronounced antibacterial action. Doses of the proposed preparation 2 to 3 times smaller than those of brufen have the same therapeutic activity in rheumatic diseases. In contrast to brufen, the preparation can be taken also during headache.

Side effects, such as discomfort in the epigastral region (1.6% of cases) and drug dermatitis in drug hypersensitive patients (2.4%), occur much more seldom when the proposed preparation is used. These symptoms pass quickly once the preparation is discontinued.

Brufen causes dyspepsia, gastrointestinal hemorrhages, bronchopspasm, thrombocytopenia, mental disorders, exacerbation of cholecystitis (11–15%), abdominal pain and headaches (11%), allergic symptoms (6–8%).

The proposed preparation is used in tablet form and may be used in the form of aerosols and ointments.

The medicinal preparation according to the invention, comprises, preferably, starch as the pharmaceutical filler. The active principle content is 0.1 to 0.2 g per tablet.

The preparation is prescribed orally, 1 to 2 tablets (0.1 to 0.2 g) at a time, three times a day, before meals. Rheumatism and polyarthritis are treated in lasting (one to one-and-a-half months long) courses. The maximum daily dose is 0.6 g.

No contraindications to the use of the proposed preparation have been established.

Medicinal forms of the proposed preparation are made by methods known in the art.

The active principle of the proposed preparation, 2,2,2-trichloro-1-(2-thiazolylamino)-ethanol, can be produced in the following way:

a dry mixture of finely reduced 2-aminothiazole and chloral hydrate, taken in equimolar quantities, are thoroughly ground and heated for two hours at a temperature of 70° C. The reaction mass is diluted with water acidified with hydrochloric acid, for the extraction of the unreacted initial products. The product remaining undissolved in the water is recrystallized from a suitable solvent, for example, isopropanol, dichloroethane, etc.

What is claimed is:

1. A method for providing antiinflammatory, analgesic and antipyretic relief to patients comprising the administration of an effective amount of an active principle consisting of 2,2,2-trichloro-1-(2-thiazolyl amino)-ethanol with the following formula:

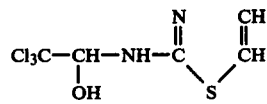

and a pharmaceutical carrier for said active principle.

2. A medicinal preparation comprising as the active principle, an effective antiinflammatory, analgesic and antipyretic amount of 2,2,2-trichloro-1-(2-thiazolyl amino)-ethanol with the following formula:

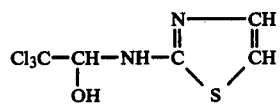

and a pharmaceutical carrier selected from the group consisting of aerosol, ointment, and starch as a filler for tablets for said active principle.

3. A medicinal preparation as claimed in claim 2, comprising starch as the pharmaceutical carrier, serving as a filler for tablets.

4. A medicinal preparation as claimed in claim 2, comprising 0.1 to 0.2 g of said active principle per tablet.

* * * * *